United States Patent

Zimmermann et al.

(10) Patent No.: US 6,964,960 B2
(45) Date of Patent: Nov. 15, 2005

(54) INDOLOQUINAZOLINONES

(75) Inventors: Kaspar Zimmermann, Oberwil (CH); Robert Portmann, Pratteln (CH); Dean Franklin Rigel, Berkeley Heights, NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 10/333,186
(22) PCT Filed: Jul. 16, 2001
(86) PCT No.: PCT/EP01/08192

§ 371 (c)(1),
(2), (4) Date: May 16, 2003

(87) PCT Pub. No.: WO02/06284

PCT Pub. Date: Jan. 24, 2002

(65) Prior Publication Data

US 2003/0199502 A1 Oct. 23, 2003

(30) Foreign Application Priority Data

Jul. 17, 2000 (GB) .............................. 0017508

(51) Int. Cl.[7] ..................... C07D 471/04; A61K 31/519
(52) U.S. Cl. ............................. 514/233.2; 514/252.16; 514/257; 544/115; 544/246
(58) Field of Search ......................... 514/233.2, 252.16, 514/257; 544/115, 246

(56) References Cited

U.S. PATENT DOCUMENTS 5,441,955 A    8/1995   Baker et al. ................. 514/250

FOREIGN PATENT DOCUMENTS

| GB | 1309 485 | 3/1973 |
|---|---|---|
| GB | 1 428 488 | 3/1976 |
| WO | WO 95 24379 | 9/1995 |

OTHER PUBLICATIONS

Abdelkarim GE, Gertz K, Harms C, Katchanov J, Dirnagl U, Szabo C, Endres M., Int J Mol Med. Mar. 2001;7(3):255–60, Medline Abstract PMID: 11179503.*

Alexander Bürkle, BioEssays vol. 23, Issue 9, pp. 795–806.*

* cited by examiner

Primary Examiner—Thomas C. McKenzie
(74) Attorney, Agent, or Firm—E. Jay Wilusz, Jr.

(57) ABSTRACT

The invention provides compounds of formula (I) wherein R is as defined in the description, and the preparation thereof. The compounds of formula (I) are useful as pharmaceuticals, for use in the treatment of any state associated with high levels of activeted PARP.

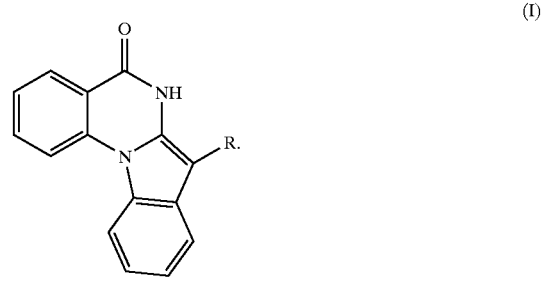

(I)

4 Claims, No Drawings

INDOLOQUINAZOLINONES

This application is a 371 of International Application PCT/EP 01/108192, filed Jul. 16, 2001.

The present invention relates to novel indoloquinazolinones, their preparation, their use as pharmaceuticals and pharmaceutical compositions containing them.

More particularly, the invention provides a compound of formula I

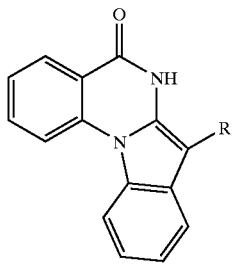

wherein
either R is —$(CH_2)_n$—X, wherein n is 1, 2 or 3 and X is $(C_{1-4})$alkyl, $(C_{1-4})$alkoxy, $(C_{2-7})$alkenyl, $(C_{2-7})$alkynyl, carboxy, $(C_{1-4})$alkoxycarbonyl, cyano, tetrazolyl, $(C_{3-7})$cycloalkylamino or imidazolyl$(C_{1-4})$alkylamino, or R is —$CH_2CON(R_1)R_2$, wherein $R_1$ and $R_2$, independently, are hydrogen, hydroxy, $(C_{1-4})$alkyl, benzyl, di$(C_{1-4})$alkylamino$(C_{1-4})$alkyl, $(C_{2-7})$alkenyl, $(C_{2-7})$alkynyl, hydroxy$(C_{1-4})$alkyl, dihydroxy $(C_{1-4})$ alkyl, cyanoalkyl, carbamoylalkyl, $(C_{3-7})$cycloalkyl, $(C_{3-7})$cycloalkyl$(C_{1-4})$alkyl, 2-oxo-3-tetrahydrofuryl, $(C_{1-4})$alkoxy$(C_{1-4})$alkyl, $(C_{1-4})$alkoxycarbonyl $(C_{3-7})$ cycloalkyl, naphthylamino$(C_{1-4})$alkyl, imidazolylamino$(C_{1-4})$alkyl, morpholinyl$(C_{1-4})$alkyl, pyrrolidinyl$(C_{1-4})$alkyl, piperidinyl$(C_{1-4})$alkyl or $(C_{3-7})$ cycloalkylamino$(C_{1-4})$alkyl, or $R_1$ and $R_2$, together with the nitrogen atom to which they are attached, form a morpholino, $(C_{1-4})$alkyl-piperazinyl, hydroxy$(C_{1-4})$ alkyl-piperazinyl, piperidinyl, pyrrolidinyl or p-chlorophenyl$(C_{1-4})$alkyl-piperazinyl, in free base or acid addition salt form.

In a further aspect, the invention provides a process for the production of the compounds of formula I and their salts, comprising the step of reacting a compound of formula II

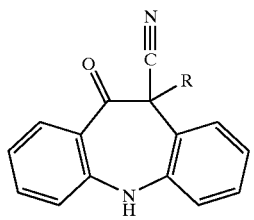

wherein R is as defined above, with sodium methoxide, and recovering the resulting compound in free base or acid addition salt form.

The reaction can be effected according to known methods, for example as described in Example 1.

Compounds of formula I obtained according to the above process can be converted into further compounds of formula I using conventional procedures, e.g. as described in Example 19 (hydrolysis of esters to acids), in Example 22 (tetrazole formation from nitrites), in Examples 25–60 (amide formation from acids), in Example 61 (reduction of esters to alcohols), in Examples 64 and 65 (reduction of nitriles to primary amines), in Example 66 (mesylation of alcohols and formation of sec. amines) or in Example 69 (formation of tert. amines).

Working up the reaction mixtures and purification of the compounds thus obtained may be carried out in accordance to known procedures.

Acid addition salts may be produced from the free bases in known manner, and vice-versa. Suitable acid addition salts for use in accordance with the present invention include for example the hydrochloride.

The starting compounds of formula II may be produced by reacting 10-oxo-10,11-dihydro-dibenzo[b,f]azepine-5-carbontrile with potassium tert.-butylate, and reacting the so obtained 11-oxo-10,11-dihydro-5H-dibenzo[b,f]azepine-10-carbonitrile with a compound of formula III wherein R is as defined above and Hal is halogen, preferably iodine or bromine.

The so obtained compound of formula II is preferably reacted in situ into the compound of formula I, for example as described in Example 1.

The starting material 10-oxo-10,11-dihydro-dibenzo[b,f] azepine-5-carbonitrile and the compounds of formula III are known or may be produced in analogous manner to known procedures.

Compounds of formula I and their pharmaceutically acceptable acid addition salts, hereinafter referred to as agents of the invention, exhibit valuable pharmacological properties when tested in vitro and in animals, and are therefore useful as pharmaceuticals.

In particular the agents of the invention inhibit the nucleic enzyme poly (adenosine 5'-diphospho-ribose) polymerase ["poly (ADP-ribose) polymerase" or PARP] as determined in in vitro assays [see for example I. U. Schraufstatter et al., J. Clin. Invest. 77, 1312–1320 (1986)] where they exhibit inhibition at concentrations of about 1 nM to about 1 $\mu$M.

The agents of the invention are therefore useful as PARP inhibitors to prevent and/or treat tissue damage resulting from cell damage or death due to necrosis or apoptosis; neural tissue damage resulting from ischemia and reperfusion injury; neurological disorders and neurodegenerative diseases such as Parkinson's disease, Alzheimer's disease, multiple sclerosis, bacterial or viral meningitis, Huntington's disease or amyotrophic lateral sclerosis; to prevent or treat vascular stroke; to treat or prevent cardiovascular disorders e.g. myocardial infarction, unstable angina, cardiac arrest during cardiopulmonary bypass or other related types of myocardial ischemic-reperfusion injury; to treat or prevent ischemic-reperfusion injury in other organs, e.g. skeletal muscle, kidney etc.; to treat other conditions and/or disorders such as age-related macular degeneration, AIDS and other immune senescence diseases, arthritis, atherosclerosis, cachexia, cancer, degenerative diseases of skeletal muscle involving replicative senescence, diabetes, head trauma, spinal cord injury, immune senescence, inflammatory bowel disorders (such as colitis and Crohn's disease), muscular dystrophy, osteoarthritis, osteoporosis, chronic and acute pain (such as neuropathic pain), renal failure, retinal ischemia, septic shock (such as endotoxic shock), and skin aging; to extend the lifespan and proliferative capacity of cells; to alter gene expression of senescent cells; or to radiosensitize hypoxic tumor cells.

The cardioprotective activity of the agents of the invention is confirmed in vivo e.g. in a model of pentobarbital-anesthetized rabbit myocardial infarction where the infarct size is reduced upon administration of about 1 to about 100 µmol/kg [For the model, see for example Ytrehus K. et al., Am. J. Physiol 267 (Heart Circ. Physiol. 36): H2383–2390, 1994 and Haessler R. et al., Cardiov. Res. 28: 1574–1580, 1994; for the cardioprotective effect of PARP inhibitors as evidenced in this model, see for example Thiemermann C. et al., Proc. Natl. Acad. Sci. USA 94: 679–683, 1997].

For the above-mentioned indications, the appropriate dosage will of course vary depending upon, for example, the compound employed, the host, the mode of administration and the nature and severity of the condition being treated. However, in general, satisfactory results in animals are indicated to be obtained at a daily dosage of from about 0.1 to about 500, preferably from about 0.5 to about 100 mg/kg animal body weight. In larger mammals, for example humans, an indicated daily dosage is in the range from about 1 to about 500, preferably from about 1 to about 300 mg of an agent of the invention, conveniently administered, for example, in divided doses up to four times a day or in sustained release form.

The agent of the invention may be administered by any conventional route, in particular enterally, preferably orally, for example in the form of tablets or capsules, or parenterally, for example in the form of injectable solutions or suspensions.

In accordance with the foregoing, the present invention also provides an agent of the invention, for use as a pharmaceutical, e.g. for the treatment of diseases indicated above.

The present invention furthermore provides a pharmaceutical composition comprising an agent of the invention in association with at least one pharmaceutical carrier or diluent. Such compositions may be manufactured in conventional manner. Unit dosage forms contain, for example, from about 0.25 to about 150, preferably from 0.25 to about 25 mg of a compound according to the invention.

Moreover the present invention provides the use of an agent of the invention, for the manufacture of a medicament for the treatment of any condition mentioned above.

In still a further aspect the present invention provides a method for the treatment of any condition mentioned above, in a subject in need of such treatment, which comprises administering to such subject a therapeutically effective amount of an agent of the invention.

The preferred compound of formula I is the 7-(1H-tetrazole-5-ylmethyl)-6H-indolol[1,2-a]quinazoline-5-one (compound of Example 22). This compound is a potent inhibitor of PARP in vitro ($IC_{50}$=12 nM). In the above-mentioned pentobarbital-anesthetized rabbit myocardial infarction model, it dose-dependently reduces infarct size when administered as a single injection at 3–70 µmol/kg i.v. (which corresponds to 0.95–22.1 mg/kg i.v. of the base) five minutes before reperfusion (60% reduction at the highest dose tested).

The following examples illustrate the invention.

EXAMPLE 1

7-Ethyl-6H-indolo[1,2-a]quinazoline-5-one

Solid potassium tert.-butylate (62.3 g, 544 mmole) is added in four portions to a solution of 10-oxo-10,11-dihydro-dibenzo[b,f]azepine-5-carbonitrile (75 g, 320 mmole) in 2.5 l of 1,2-dichloroethane at r.t. within 2 h. Thereafter a mixture of acetic acid (32.2 ml) and 300 ml ice-cold water is slowly added. The resulting suspension is stirred for 10 min., cyclohexan (650 ml) is added and stirring is continued for 1 h at 0° C. The precipitate is collected by filtration, washed with water (300 ml) and cyclohexane (300 ml). The so obtained 11-oxo-10,11-dihydro-5H-dibenzo[b,f]azepine-10-carbonitrile (pale-yellow crystals) is recrystallized from 2.5 l boiling EtOH upon concentration to 1.2 l and slow cooling. m.p.: 195–197° C.; ES-MS(+): 235 (M+1); $^1$H-NMR (CDCl$_3$, 200 MHz): 4.90 (s, 1H); 6.81 (s br, 1H); 6.95–7.18 (m, 3H); 7.29–7.35 (m, 2H); 7.49 (td, 1H); 7.65 (dd, 1H); 8.01 (dd, 1H).

A mixture of 11-oxo-10,11-dihydro-5H-dibenzo[b,f]azepine-10-carbonitrile (500 mg, 2.13 mmol), potassium carbonate (359 mg, 2.6 mmole) and ethyl iodide (0.202 ml, 2.5 mmole) in 4 ml DMF is stirred at r.t. for 18 h.

After removal of solid particles, methanolic sodium methoxide solution (2 ml, 5.4 M) is added, followed by heating at 65° C. for 5 h. The mixture is poured into ice-water (40 ml) containing 1 ml AcOH, extracted with dichloromethane (3×40 ml), and the organic layers are dried using MgSO$_4$, then evaporated. 7-Ethyl-6H-indolo[1,2a]quinazoline-5-one (323.3 mg, 58%) crystallizes spontaneously from EtOH as pale-yellow platelets. m.p.: 245–260° C.; ES-MS(+): 263 (M+1); $^1$H-NMR (d$_6$-DMSO, 300 MHz): 1.12 (t, 3H); 2.81 (q, 2H); 7.19–7.29 (m, 3H); 7.39 (t, 1H); 7.58 (d, 1H); 7.84 (t, 1H); 8.19 (d, 1H); 8.27 (d, 1H); 8.41 (d, 1H); 11.55 (s br, 1H).

The following compounds of formula I are prepared analogously to Example 1:

| Ex | R | Characterization |
|---|---|---|
| 2 | CH$_3$ | yellow crystals. m.p.: >260° C. ES-MS(+): 248 (M + 1) |
| 3 | CH$_2$CH$_2$CH$_3$ | pale-yellow crystals. m.p.: 245–250° C. ES-MS(+): 277 (M + 1) |
| 4 | CH$_2$CH$_2$CH$_2$CH$_3$ | pale-yellow crystals. m.p.: 247–249° C. ES-MS(+): 291 (M + 1) |
| 5 | CH(CH$_3$)$_2$ | yellow crystals. m.p.: 238–240° C. ES-MS(+): 277 (M + 1) |
| 6 | CH$_2$CH(CH$_3$)$_2$ | yellow crystals. m.p.: 260–268° C. ES-MS(+): 291 (M + 1) |
| 7 | CH(CH$_3$)CH$_2$CH$_3$ | pale-yellow crystals. m.p.: 207–220° C. ES-MS(+): 291 (M + 1) |
| 8 | CH$_2$CH=CH$_2$ | pale-yellow crystals. m.p.: 247–259° C (dec.) ES-MS(+): 275 (M + 1) |
| 9 | CH$_2$CH$_2$C$_6$H$_5$ | yellow crystals. m.p.: 292–302° C. ES-MS(+): 339 (M + 1) |
| 10 | CH$_2$C$_6$H$_5$ | yellow crystals. m.p.: 241 –249° C. ES-MS(+): 325 (M + 1) |
| 11 | CH$_2$C≡CH | yellow crystals. m.p.: 208–210° C. ES-MS(+): 273 (M + 1) |
| 12 | CH$_2$COOCH$_3$ | yellow crystals. m.p.: > 220° C. (dec.). ES-MS(+): 306 (M + 1) |
| 13 | CH$_2$CH$_2$COOCH$_3$ | yellow crystals. m.p.: 269–270° C. ES-MS(+): 321 (M + 1) |
| 14 | CH$_2$CH$_2$CH$_2$COOCH$_3$ | yellow crystals. m.p.: 253–254° C. ES-MS(+): 335 (M + 1) |
| 15 | CH$_2$CN | off-white solid. m.p.: 283–290° C. (dec.). ES-MS(+): 274 (M + 1) |
| 16 | CH$_2$CH$_2$CN | yellow crystals. m.p.: 285–299° C (dec.). ES-MS(+): 288 (M + 1) |
| 17 | CH$_2$CH$_2$CH$_2$CN | yellow crystals. m.p.: dec. >230° C. ES-MS(+): 302 (M + 1) |
| 18 | CH$_2$CH$_2$OCH$_3$ | yellow crystals, obtained after alkylation reaction with |

| Ex | R | Characterization |
|---|---|---|
| | 1-bromo-2-chloro-ethane. | m.p.: 172–182° C. ES-MS(+): 293 (M + 1) |

EXAMPLE 19

(5-Oxo-5,6-dihydro-indolo[1,2-a]quinazoline-7-yl) acetic acid

A suspension of (5-Oxo-5,6-dihydro-indolo[1,2a] quinazoline-7-yl) methyl acetate (5.0 g, 16.32 mmole, Example 12) in DMSO (50 ml) is treated with 1N aqueous sodium hydorixyde solution. The mixture is diluted with water (150 ml) and the free acid (yellow crystals) brought to precipitation by addition of acetic acid (20 ml). m.p.: dec.>190° C.; ES-MS(+): 291 (M+1); $^1$H-NMR (d$_6$-DMSO, 200 MHz): 3.83 (s, 2H); 7.21–7.30 (m, 2H); 7.35–7.52 (m, 2H); 7.85 (td, 1H); 8.15–8.30 (m, 2H); 8.42 (d, 1H).

The following compounds of formula I are prepared analogously to Example 19:

| Ex | R | Characterization |
|---|---|---|
| 20 | CH$_2$CH$_2$COOH | yellow crystals. m.p.: 288–290° C. ES-MS(−): 305 (M − 1) |
| 21 | CH$_2$CH$_2$CH$_2$COOH | yellow crystals. m.p.: 272–276° C. ES-MS(−): 319 (M − 1) |

EXAMPLE 22

7-(1 H-Tetrazole-5-ylmethyl)-6H-indolo[1,2-a] quinazoline-5-one

A solution of (5-oxo-5,6-dihydro-indolo[1,2a] quinazoline-7-yl)-acetonitrile (1.2 g, 4.39 mmole) (Example 15), sodium azide (856.4 mg, 13.2 mmole) and triethylamine hydrochloride (907 mg, 6.6 mmole) in 1-methyl-2-pyrrolidone (30 ml) is heated at 100° C. for 18 h. The mixture is poured into ice-water (500 ml), acidified to pH 1 with 2N hydrochloric acid and stirred for 15 min. The product is extracted with ethyl acetate, the organic layers are washed with water and brine, dried using MgSO$_4$, filtered, and evaporated. The remaining solid is precipitated from MeOH with hexane giving a brownish solid. m.p.: 262–265° C.; ES-MS(−): 315 (M−1); $^1$H-NMR (d$_6$-DMSO, 300 MHz): 4.52 (s, 2H); 7.16–7.30 (m, 2H); 7.38 (t, 1H); 7.52–7.58 (m, 1H); 7.85 (t, 1H); 8.15–8.30 (m, 2H); 8.42 (d, 1H).

The following compounds of formula I are prepared analogously to Example 22:

| Ex | R | Characterization |
|---|---|---|
| 23 | CH$_2$CH$_2$-tetrazole | pale off-white crystals. m.p.: 289–291° C. ES-MS(−): 329 (M − 1) |
| 24 | CH$_2$CH$_2$CH$_2$-tetrazole | yellow crystals. m.p.: 256–260° C. ES-MS(−): 343 (M − 1) |

EXAMPLES 25–60

Parallel synthesis of 7-acetamido-6H-indolo[1,2-a] quinazoline-5-one derivatives In a parallel synthesis set-up on a 0.1 mmol scale (5-Oxo-5,6-dihydro-indolo[1,2a]quinazoline-7-yl) acetic acid (Example 19) is pre-activated with N-(3-dimethylaminopropyl)-N'-ethyl-carbodiimide-hydrochloride (EDC) and 1-hydroxy-benzotriazole (HOBt) in 1-methyl-2-pyrrolidone, then divided into 25 parts and added to primary or secondary amines. Triethylamine is used as an additional base in order to trap HCl from EDC and in case the hydrochloride salts of the amines are used. (Molar ratios: acid: 0.1 mmol; EDC, HOBt: 2 eq.; Et$_3$N: 4 eq. amine: 1.0 eq.). After 18 h of shaking, the reaction mixtures are filtered (0.45μ syringe filters) and directly injected into a preparative HPLC (reverse phase C-18). The largest peaks at 254 nm are collected, the solvents evaporated and the product analyzed by electrospray-MS. In most cases, the product directly crystallizes during evaporation of the solvents. The solid products are dried in vacuo at 80° C. for 18 h.

| Ex | NR1R2 | Characterization |
|---|---|---|
| 25 | morpholino | yellow crystals. ES-MS(+): 362 (M+1) |
| 26 | NHEt | yellow crystals. ES-MS(+): 320 (M+1) |
| 27 | NH$_2$ | yellow crystals. ES-MS(+): 292 (M+1) |
| 28 | 4-Me-1-piperazinyl | yellow crystals. ES-MS(+): 375 (M+1) |
| 29 | 1-piperidinyl | yellow crystals. ES-MS(+): 360 (M+1) |
| 30 | 1-pyrrolidinyl | yellow crystals. ES-MS(+): 346 (M+1) |
| 31 | N(CH$_3$)$_2$ | yellow crystals. ES-MS(+): 320 (M+1) |
| 32 | N-Me-benzyl | yellow crystals. ES-MS(+): 396 (M+l) |
| 33 | NHCH$_2$CH$_2$NMe$_2$ | yellow crystals. m.p.: 236–240° C. (dec.); ES-MS(+): 363 (M+1) |
| 34 | NHCH$_3$ | yellow crystals. m.p.: >325° C. (dec.); ES-MS(+): 305 (M+1) |
| 35 | NH-propargyl | yellow crystals. ES-MS(+): 330 (M+1) |
| 36 | NH-allyl | yellow crystals. ES-MS(+): 332 (M+1) |
| 37 | NH-n-propyl | yellow crystals. ES-MS(+): 334 (M+1) |
| 38 | N-Me-propargyl | yellow crystals. ES-MS(+): 344 (M+1) |
| 39 | NHCH$_2$CH$_2$OH | yellow crystals. m.p.: 274–280° C. (dec.); ES-MS(+): 336 (M+1) |
| 40 | NHCH$_2$CH$_2$CH$_2$OH | yellow crystals. m.p.: 271–280° C. (dec.); ES-MS(+): 350 (M+1) |
| 41 | NHCH$_2$CN | yellow crystals. ES-MS(+): 331 (M+1) |
| 42 | NHCH$_2$CONH$_2$ | yellow crystals. m.p.: 297–299° C. (dec.); ES-MS(+): 349 (M+1) |
| 43 | NHCH$_2$-cyclopropyl | yellow crystals. ES-MS(+): 346 (M+1) |
| 44 | NHCH$_2$CH(OH)—CH$_2$OH | yellow solid. m.p.: 297-299° C. (dec.); ES-MS(+): 366 (M+1) |
| 45 |  | yellow crystals. m.p.: 276–281° C. (dec.); ES-MS(+): 376 (M+1) |
| 46 | NH-cyclopropyl | yellow solid. m.p.: 297–302° C. (dec.); ES-MS(+): 332 (M+1) |
| 47 | NHCH$_2$CH$_2$OCH$_3$ | yellow solid. m.p.: 262–273° C. (dec.); ES-MS(+): 350 (M+1) |
| 48 | 4-CH$_2$CH$_2$OH-1-piperazinyl | yellow solid. ES-MS(+): 405 (M+1) |
| 49 | NH COOCH$_3$ | yellow crystals. ES-MS(+): 389 (M+1) |

-continued

| Ex | NR1R2 | Characterization |
|---|---|---|
| 50 | p-Cl-phenyl-piperazinyl-4-ethyl | yellow solid. ES-MS(+): 500 (M+1) |
| 51 | NHOH | yellow powder. ES-MS(+): 306 (M+1) |
| 52 | NHCH$_2$CH$_2$NH-2-naphthyl | brown solid. ES-MS(+): 461 (M+1) |
| 53 | NHCH$_2$CH$_2$NH-4-imidazolyl | brown solid. ES-MS(+): 386 (M+1) |
| 54 | NHCH$_2$CH$_2$-morpholino | brown solid. ES-MS(+): 405 (M+1) |
| 55 | NHCH$_2$CH$_2$-1-pyrrolidinyl | brown solid. ES-MS(+): 389 (M+1) |
| 56 | NHCH$_2$CH$_2$-1-piperidinyl | brown solid. ES-MS(+): 403 (M+1) |
| 57 | NHCH$_2$CH$_2$CH$_2$-morpholino | brown solid. ES-MS(+): 419 (M+1) |
| 58 | NHCH$_2$-4-piperidinyl | green solid. ES-MS(+): 389 (M+1) |
| 59 | NHCH$_2$CH$_2$CH$_2$NH-cyclohexyl | brown solid. ES-MS(+): 431 (M+1) |
| 60 | NHCH$_2$CH$_2$CH$_2$NMe$_2$ | brown solid. ES-MS(+): 377 (M+1) |

EXAMPLE 61

7-(2-Hydroxy-ethyl)-6H-indolo[1,2-a]quinazoline-5-one

A THF (25 ml) solution of lithium borohydride (0.62 g, 28.56 mmole) is added dropwise to a suspension of (5-oxo-5,6-dihydro-indolo[1,2-a]quinazoline-7-yl) methyl acetate (2.5 g, 8.16 mmol) (Example 12) in THF (40 ml) at r.t. The reaction mixture is heated at 75° C. for 18 h. Then ethanol (100 ml) and water (20 ml) are added after cooling to 10° C. After 15 min. the mixture is chilled to 0° C. and acidified (pH 7) with 2N hydrochloric acid, giving a thick yellow suspension. The product (1.6 g, 71%) is collected by filtration, washed with water and ethanol and dried in vacuo at 60° C. m.p.: 248–252° C. ES-MS(+): 279 (M+1); $^1$H-NMR (d$_6$-DMSO, 200 MHz): 1.15 (s br, 1H); 2.90 (t, 2H); 3.60 (t, 2H); 7.15–7.30 (m, 2H); 7.38 (t, 1H); 7.53–7.61 (m, 1H); 7.85 (td, 1H); 8.13–8.31 (m, 2H); 8.43 (d, 1H).

The following compounds of formula I are prepared analogously to Example 61:

| Ex | R | Characterization |
|---|---|---|
| 62 | CH$_2$CH$_2$CH$_2$OH | yellow crystals. m.p.: 255–257° C. ES-MS(+): 293 (M + 1) |
| 63 | CH$_2$CH$_2$CH$_2$CH$_2$OH | yellow crystals. m.p.: 259–264° C. ES-MS(+): 307 (M + 1) |

EXAMPLE 64

7-(2-Amino-ethyl)-6H-indolo[1,2-a]quinazoline-5-one (5-Oxo-5,6-dihydro-indolo[1,2-a]quinazoline-7-yl)-acetonitrile (0.5 g, 1.83 mmol) (example 15) is dissolved in DMF (25 ml) and MeOH with 10% NH$_3$ (25 ml) and catalytically hydrogenolized with Raney-Nickel (0.2 g) in ethanol at 50° C. for 9 h. The catalyst is removed by filtration. The product spontaneously crystallizes from the filtrate giving 0.23 mg (46%) slightly greenish crystals. m.p.: >300° C. ES-MS(+): 278 (M+1).

EXAMPLE 65

7-(2-Amino-butyl)-6H-indolo[1,2-a]quinazoline-5-one

This compound is prepared in analogy to Example 64 using (5-Oxo-5,6-dihydro-indolo[1,2-a]quinazoline-7-yl)-butyronitril (Example 17) as starting material. m.p.: 165–195° C. (dec.). ES-MS(+): 306 (M+1).

EXAMPLE 66

7-[2-(2-Morpholin-4-yl-ethylamino)-ethyl]-6H-indolo[1,2-a]quinazoline-5-one di-hydrochloride salt 2-(5-Oxo-5,6-dihydro-indolo[1,2-a]quinazoline-7-yl)-ethyl methanesulfonate is prepared from 7-(2-hydroxy-ethyl)-6H-indolo[1,2a]quinazoline-5-one in pyridine at 0° C. upon addition of methane sulfochloride. To a solution of the resulting methanesulfonate (0.2 g, 0.56 mmol) in 1-methyl-2-pyrrolidone (2 ml), 4-(2-aminoethyl)morpholine (0.11 ml, 0.84 mmole) is added at r.t., followed by heating at 65° C. for 4 h. After cooling, water (15 ml) is added and the product extracted with dichloromethane. The organic layers are washed with water and brine, dried with MgSO$_4$, and the solvent is evaporated. The resulting oil is dissolved in methanol. 1N HCl in ethanol addition leads to crystallization of the di-hydrochloride salt. m.p.: 196–198° C. ES-MS(+): 391 (M+1).

The following compounds of formula I are prepared analogously to Example 66:

| Ex | R | Characterization |
|---|---|---|
| 67 | CH$_2$CH$_2$NH-cyclopropyl, hydrochloride | brown crystals. m.p.: 190–192° C. ES-MS(+): 318 (M + 1) |
| 68 | CH$_2$CH$_2$NHCH$_2$CH$_2$-imidazole-4-yl (free base) | brown crystals. m.p.: 88–92° C. ES-MS(+): 372 (M + 1) |

EXAMPLE 69

7-[2-(2-Oxo-pyrrolidine-1-yl)-ethyl]-6H-indolo[1,2-a]quinazoline-5-one

Pyrrolidone (0.131 ml, 1.71 mmole) is added dropwise to sodium hydride (0.048 g, 1.11 mmole, 55% oily suspension) in DMF (1 ml) at 0° C. followed by addition of 2-(5-oxo-5,6-dihydro-indolo[1,2-.a.]quinazoline-7-yl)-ethyl methanesulfonate (0.304 g, 0.85 mmole, prepared as described in example 67) and stirring at r.t. overnight. Ice-water (80 ml) is added and the mixture extracted with tert.-butyl-methyl ether. The organic layers are washed with water and brine, dried over MgSO$_4$, filtered, and the solvent is evaporated. The remainder is purified by preparative reverse-phase (C-18) HPLC. m.p.: 154–155° C. ES-MS(+): 347 (M+1).

What is claimed is:

1. A compound of formula

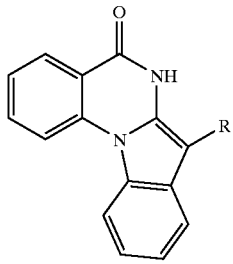

I wherein
either R is —(CH$_2$)$_n$—X, wherein n is 1, 2 or 3 and X is (C$_{1-4}$)alkyl, (C$_{1-4}$)alkoxy, (C$_{2-7}$)alkenyl, carboxy, (C$_{1-4}$)alkoxycarbonyl, cyano, tetrazolyl, (C$_{3-7}$)cycloalkylamino or imidazolyl(C$_{1-4}$)alkylamino,
or R is —CH$_2$CON(R$_1$)R$_2$, wherein R$_1$ and R$_2$, independently, are hydrogen, hydroxy, (C$_{1-4}$)alkyl, benzyl, di(C$_{1-4}$)alkylamino(C$_{1-4}$)alkyl, (C$_{2-7}$)alkenyl, (C$_{2-7}$)alkynyl, hydroxy(C$_{1-4}$)alkyl, dihydroxy (C$_{1-4}$) alkyl, cyanoalkyl, carbamoylalkyl, (C$_{3-7}$)cycloalkyl, (C$_{3-7}$)cycloalkyl(C$_{1-4}$)alkyl, 2-oxo-3-tetrahydrofuryl, (C$_{1-4}$)alkoxy(C$_{1-4}$)alkyl, (C$_{1-4}$)alkoxycarbonyl (C$_{3-7}$) cycloalkyl, naphthylamino(C$_{1-4}$)alkyl, imidazolylamino(C$_{1-4}$)alkyl, morpholinyl(C$_{1-4}$)alkyl, pyrrolidinyl(C$_{1-4}$)alkyl, piperidinyl(C$_{1-4}$)alkyl or (C$_{3-7}$) cycloalkylamino(C$_{1-4}$)alkyl, or R$_1$ and R$_2$, together with the nitrogen atom to which they are attached, form a morpholino, (C$_{1-4}$)alkylpiperazinyl, hydroxy(C$_{1-4}$) alkyl-piperazinyl, piperidinyl, pyrrolidinyl or p-chlorophenyl(C$_{1-4}$)alkyl-piperazinyl, in free base or acid addition salt form.

2. 7-(1H-Tetrazole-5-ylmethyl)-6H-indolo[1,2-a] quinazoline-5-one in free base or acid addition salt form.

3. A pharmaceutical composition comprising a compound of claim 1 in free base or pharmaceutically acceptable acid addition salt form, in association with a pharmaceutical carrier or diluent.

4. A process for the preparation of a compound of formula I as defined in claim 1, or a salt thereof, comprising the step of reacting a compound of formula II

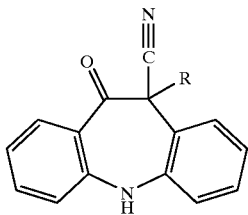

II wherein R is as defined in claim 1, with sodium methoxide, and recovering the resulting compound in free base of acid addition salt form.

* * * * *